US006268400B1

(12) United States Patent
Amalric et al.

(10) Patent No.: US 6,268,400 B1
(45) Date of Patent: *Jul. 31, 2001

(54) COMPOSITIONS BASED ON ALKYL POLYGLYCOSIDES AND FATTY ALCOHOLS, USEFUL ESPECIALLY FOR PREPARING STABLE FLUID EMULSIONS

(75) Inventors: Chantal Amalric, Blan; Guy Tabacchi; Jean-Pierre Boiteux, both of Castres; Nelly Michel, Maisons Alfort; Alain Milius, Nice, all of (FR)

(73) Assignee: Societe d'Exploitation de Produits pour les Industries Chimiques-Seppic, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 09/422,981

(22) Filed: Oct. 22, 1999

(30) Foreign Application Priority Data

Oct. 22, 1998 (FR) .................................... 98 13255

(51) Int. Cl.⁷ .............................. B01F 17/56; A61K 7/02; A61K 7/42; C11D 3/22
(52) U.S. Cl. ........................... 516/72; 510/417; 510/470; 514/844; 514/846; 514/938; 514/975; 516/74
(58) Field of Search .................. 516/72, 74; 514/844, 514/846, 938, 975; 510/470, 417

(56) References Cited

U.S. PATENT DOCUMENTS

| | | | |
|---|---|---|---|
| 4,749,517 | * | 6/1988 | Chwang et al. ................. 514/844 X |
| 4,889,925 | * | 12/1989 | Schmid et al. .................. 514/844 X |
| 5,166,194 | * | 11/1992 | Walker et al. ................... 514/975 X |
| 5,494,938 | * | 2/1996 | Kawa et al. ..................... 514/844 X |
| 5,510,100 | * | 4/1996 | Picard et al. .................... 514/938 X |
| 5,605,651 | * | 2/1997 | Balzer .............................. 516/72 X |
| 5,670,471 | * | 9/1997 | Amalric et al. ................... 510/416 |
| 5,817,254 | * | 10/1998 | Wadle et al. .................... 516/72 X |
| 5,888,482 | * | 3/1999 | Amalric et al. .................. 516/72 X |
| 5,958,431 | * | 9/1999 | Brancq et al. .................. 514/938 X |

* cited by examiner

Primary Examiner—Richard D. Lovering
(74) Attorney, Agent, or Firm—Dennison, Scheiner, Schultz & Wakeman

(57) ABSTRACT

The present invention relates to compositions based on alkyl polyglycosides and fatty alcohols which enable stable fluid emulsions to be produced, and which contain These compositions generally comprise:

5 to 60% by weight of a mixture of alkyl polyglycosides essentially consisting of:

10 to 25% by weight of an alkyl polyglycoside of formula (I)

$$R_1O(G_1)_{x_1} \quad (I)$$

10 to 30% by weight of an alkyl polyglycoside of formula (II)

$$R_2O(G_2)_{x_2} \quad (II)$$

0 to 10% by weight of a mixture of alkyl polyglycosides of formulae (III) and (IV):

$$R_3O(G_3)_{x_3} \quad (III)$$

$$R_4O(G_4)_{x_4} \quad (IV)$$

40 to 80% by weight of a mixture of alkyl polyglycosides of formulae (V) and (VI):

$$R_5O(G_5)_{x_5} \quad (V)$$

$$R_6O(G_6)_{x_6} \quad (VI)$$

in which $R_1$, $R_2$, $R_3$, $R_4$, $R_5$ and $R_6$ each represent a linear or branched aliphatic radical having 12, 14, 16, 18, 20 and 22 carbon atoms respectively, $G_1$, $G_2$, $G_3$, $G_4$, $G_5$ and $G_6$ each represent a saccharide residue, $x_1$, $x_2$, $x_3$, $x_4$, $x_5$ and $x_6$ each represent a number between 1 and 5;

95 to 40% by weight of one or more alcohols of formula R'OH, in which R' is a linear or branched aliphatic radical having 12 to 22 carbon atoms, and preferably of a mixture consisting of alcohols the alkyl part of which is identical to the alkyl part $R_1$, $R_2$, $R_3$, $R_4$, $R_5$ and $R_6$ of the alkyl polyglycosides mentioned above.

7 Claims, No Drawings

COMPOSITIONS BASED ON ALKYL POLYGLYCOSIDES AND FATTY ALCOHOLS, USEFUL ESPECIALLY FOR PREPARING STABLE FLUID EMULSIONS

BACKGROUND OF THE INVENTION

The present invention relates to a novel family of compositions based on alkyl polyglycosides and fatty alcohols, which are useful especially for preparing stable, fluid emulsions.

The invention is especially applicable in the cosmetic field.

Alkyl glycosides or alkyl polyglycosides (APG) are well-known non-ionic surface-active compounds which can be used on their own, or in association with other surfactants, in a broad range of industrial applications and especially in the cosmetics sector.

Alkyl polyglycosides were first used as foaming agents and, in this application, those with an alkyl chain containing from 8 to 14 carbon atoms were found to be of particular value.

More recently, alkyl polyglycosides have been used as emulsifiers and, in this application, those with an alkyl chain containing from 16 to 18 carbon atoms have proved to be of particular value.

Patent application WO 92/06778, in the name of the Applicant, describes for the first time the use of mixtures of alkyl polyglycosides and fatty alcohols as self-emulsifying agents.

<<Self-emulsifying>> designates any agent or composition which is capable of forming a stable emulsion with an aqueous phase, practically without the provision of energy, for example by dispersion in the aqueous phase by slow, mechanical agitation.

More specifically, the mixtures described in this prior art document comprise:
- 60 to 90% by weight of at least one fatty alcohol having 12 to 22 carbon atoms, and preferably 16 to 18 carbon atoms; and
- 10 to 40% by weight of an alkyl polyglycoside, the alkyl part of which is preferably identical to that of the fatty alcohol.

The self-emulsifiable compositions described in the patent application cited above are marketed under the name Montanov® 68 and contain a mixture of alkyl polyglycosides whose fatty chains contain 16 and 18 carbon atoms, and a mixture of fatty alcohols with the same length of fatty chains.

Although such compositions are perfectly satisfactory, especially in terms of the stability of the emulsions obtainable therewith, these emulsions do not however enable fluid emulsions to be obtained easily.

Furthermore, International patent application WO 95/13863, in the name of the Applicant, also describes compositions based on alkyl polyglycosides and fatty alcohols, which are in the form of concentrates, which enable the preparation of fluid emulsions.

These compositions are essentially characterised by the fact that they comprise a mixture of at least two alkyl polyglycosides which differ in the nature of their alkyl part, at least one of these alkyl polyglycosides containing an alkyl chain having 16 to 22 carbon atoms, and preferably 16 to 18 carbon atoms and representing at least 25%, and preferably at least 50% by weight, of the mixture of alkyl polyglycosides.

Although the compositions described in this prior art document are satisfactory as regards the fluidity of the emulsions obtainable therewith, it has been observed that these emulsions are not entirely satisfactory from the point of view of their stability.

In practice, it is generally necessary to employ such compositions at a high use amount, or in association with a co-surfactant or with a stabiliser.

SUMMARY OF THE INVENTION

Under these conditions, the object of the present invention is to solve the technical problem which consists in providing novel compositions which in low amounts enable the preparation of stable, fluid emulsions, without using a co-surfactant or a stabiliser.

It has been discovered, and this constitutes the basis of the present invention, that certain particular mixtures of alkyl polyglycosides and fatty alcohols enable meeting the objective sought after.

Thus, the solution in accordance with the present invention for solving the technical problem mentioned above consists of novel compositions based on alkyl polyglycosides and fatty alcohols, characterised in that they comprise:

5 to 60% by weight of a mixture of alkyl polyglycosides essentially consisting of:

10 to 25% by weight of an alkyl polyglycoside of formula (I):

$$R_1O(G_1)_{x_1} \qquad (I)$$

10 to 30% by weight of an alkyl polyglycoside of formula (II):

$$R_2O(G_2)_{x_2} \qquad (II)$$

0 to 10% by weight of a mixture of alkyl polyglycosides of formulae (III) and (IV):

$$R_3O(G_3)_{x_3} \qquad (III)$$

$$R_4O(G_4)_{x_4} \qquad (IV)$$

40 to 80% by weight of a mixture of alkyl polyglycosides of formulae (V) and (VI):

$$R_5O(G_5)_{x_5} \qquad (V)$$

$$R_6O(G_6)_{x_6} \qquad (VI)$$

in which $R_1$, $R_2$, $R_3$, $R_4$, $R_5$ and $R_6$ each represent a linear or branched aliphatic radical having 12, 14, 16, 18, 20 and 22 carbon atoms respectively, $G_1$, $G_2$, $G_3$, $G_4$, $G_5$ and $G_6$ each represent a saccharide residue, $x_1$, $x_2$, $x_3$, $x_4$, $x_5$ and $x_6$ each represent a number between 1 and 5;

95 to 40% by weight of one or more alcohols of formula R'OH, in which R' is a linear or branched aliphatic radical having 12 to 22 carbon atoms, and preferably of a mixture consisting of alcohols the alkyl part of which is identical to the alkyl part $R_1$, $R_2$, $R_3$, $R_4$, $R_5$ and $R_6$ of the alkyl polyglycosides mentioned above.

DETAILED DESCRIPTION OF THE INVENTION

The novel compositions based on alkyl polyglycosides and fatty alcohols which have just been defined enable, in an entirely unexpected manner, the preparation of stable, fluid emulsions without using a co-surfactant or a stabiliser, and this even at relatively low use amounts.

Within the framework of the present application, «fluid emulsion» is understood as meaning an emulsion the running of which through an ISO 2431 running cut of 6 min commences less than 5 seconds after removing the shutter (test according to the International Standard ISO 243o1).

Milks, particularly milks of the oil-in-water type, for cosmetic or hygiene use, such as, for example, make-up removing milks, body milks, or solar milks, can especially be cited as fluid emulsions.

A preferred sub-family of compositions based on alkyl polyglycosides and fatty alcohols which can be used within the framework of the present invention consists of compositions the mixture of alkyl polyglycosides of which essentially consists of:

10 to 20% by weight of an alkyl polyglycoside of formula (I):

$$R_1O(G_1)_{x_1} \tag{I}$$

15 to 25% by weight of an alkyl polyglycoside of formula (II):

$$R_2O(G_2)_{x_2} \tag{II}$$

0 to 10% by weight of a mixture of alkyl polyglycosides of formulae (III) and (IV):

$$R_3O(G_3)_{x_3} \tag{III}$$

$$R_4O(G_4)_{x_4} \tag{IV}$$

50 to 70% by weight of a mixture of alkyl polyglycosides of formulae (V) and (VI):

$$R_5O(G_5)_{x_5} \tag{V}$$

$$R_6O(G_6)_{x_6} \tag{VI}$$

in which $R_1$, $R_2$, $R_3$, $R_4$, $R_5$, $R_6$, $G_1$, $G_2$, $G_3$, $G_4$, $G_5$, $G_6$, $x_1$, $x_2$, $x_3$, $x_4$, $x_5$ and $x_6$ are as defined above.

The preferred compositions within the framework of the present invention are the compositions comprising:

10 to 40% by weight of a mixture of alkyl polyglycosides as defined above, 90 to 60% by weight of one or more alcohols as defined above.

A particularly preferred composition within the framework of the present invention consists of:

19.9% by weight of a mixture of alkyl polyglycosides essentially consisting of:

17% by weight of an alkyl polyglycoside of formula (I):

$$R_1O(G_1)_{x_1} \tag{I}$$

19% by weight of an alkyl polyglycoside of formula (II):

$$R_2O(G_2)_{x_2} \tag{II}$$

5% by weight of a mixture of alkyl polyglycosides of formulae (III) and (IV):

$$R_3O(G_3)_{x_3} \tag{III}$$

$$R_4O(G_4)_{x_4} \tag{IV}$$

59% by weight of a mixture of alkyl polyglycosides of formulae (V) and (VI):

$$R_5O(G_5)_{x_5} \tag{V}$$

$$R_6O(G_6)_{x_6} \tag{VI}$$

in which $R_1$, $R_2$, $R_3$, $R_4$, $R_5$ and $R_6$ each represent a linear or branched aliphatic radical having 12, 14, 16, 18, 20 and 22 carbon atoms respectively, $G_1$, $G_2$, $G_3$, $G_4$, $G_5$ and $G_6$ each represent a saccharide residue, $x_1$, $x_2$, $x_3$, $x_4$, $x_5$ and $x_6$ each represent a number between 1 and 5;

80.1% by weight of one or more alcohols of formula R'OH, in which R' is a linear or branched aliphatic radical having 12 to 22 carbon atoms, and preferably of a mixture consisting of alcohols the alkyl part of which is identical to the alkyl part $R_1$, $R_2$, $R_3$, $R_4$, $R_5$ and $R_6$ of the alkyl polyglycosides mentioned above.

The alkyl polyglycosides of formulae (I), (II), (III), (IV), (V) and (VI) mentioned above can contain, as saccharide residue represented by $G_1$, $G_2$, $G_3$, $G_4$, $G_5$ and $G_6$ respectively, a residue of glucose or dextrose, fructose, galactose, maltose, maltotriose, lactose, cellobiose, mannose, ribose, dextran, talose, allose, xylose, levoglucosan, cellulose or starch.

Advantageously, $G_1$, $G_2$, $G_3$, $G_4$, $G_5$ and $G_6$ each represent a glucose residue.

It should also be noted that each unit of the polyoside moiety of the alkyl polyglycoside can be in the α or β anomeric form and the saccharide residue can be of the furanoside or pyranoside type.

The indices $x_1$, $x_2$, $x_3$, $x_4$, $x_5$ and $x_6$ represent the mean degree of polymerisation of the saccharide residue. These indices will preferably represent a number between 1.05 and 2.5 and particularly preferably between 1.1 and 2.

The expression «alkyl polyglycoside» used within the framework of the present application therefore arbitrarily denotes alkyl monoosides (degree of polymerisation equal to 1) or alkyl polyglycosides (degree of polymerisation greater than 1).

The alkyl polyglycosides of formulae (I), (II), (III), (IV), (V) and (VI) are compounds whose alkyl radicals have chains of determinate length. However, these compounds can also contain minor proportions of compounds of the same nature whose alkyl radicals have a longer and/or shorter chain, such compounds originating especially from the fatty alcohols, generally of natural or synthetic origin, used as starting materials for the synthesis of these alkyl polyglycosides.

The expression «essentially consisting of» used within the framework of the present patent application and the claims in order to characterise the above-mentioned mixture of alkyl polyglycosides, must therefore be understood not to exclude the presence, in the mixture of alkyl polyglycosides, of compounds whose alkyl radicals have 10 or 24 carbon atoms, in a maximum cumulative amount of 5% by weight and preferably 1% by weight, based on the total weight of the mixture of alkyl polyglycosides.

The compositions according to the present invention based on alkyl polyglycosides and fatty alcohols can be prepared simply by mixing their constituents in desired predetermined proportions.

On the industrial scale they will preferably be prepared by one of the two methods conventionally used for the synthesis of alkyl polyglycosides, for example by reacting a fatty alcohol with a saccharide containing an anomeric OH, such as glucose or dextrose, in an acid medium.

Such methods of synthesis are well known and have been described in numerous documents, particularly in the Applicant's documents referred to above.

If necessary, this synthesis may be completed with operations involving neutralisation, filtration, partial distillation or extraction of the excess fatty alcohol, or decolorization.

The compositions according to the present invention based on alkyl polyglycosides and fatty alcohols can be used as the main emulsifier for the preparation of a variety of fluid emulsions.

Thus, according to a second aspect, the present patent application aims to cover fluid emulsions comprising at least an aqueous phase and an oily phase and, as the main emulsifier, a composition based on alkyl polyglycosides and fatty alcohols, as defined above.

In general terms, such an emulsion will comprise from 1 to 25% by weight, preferably from 1 to 10% by weight and more preferably 3% by weight of the above-mentioned composition.

The oily phase constituting the emulsion can consist of the fatty alcohol or fatty alcohols constituting the emulsifying composition of the invention, without it being necessary to use another oil. More generally, however, an oil selected from the following will be used:

oils of plant origin, such as sweet-almond oil, coconut oil, castor oil, jojoba oil, olive oil, rapeseed oil, groundnut oil, sunflower oil, wheat germ oil, maize germ oil, soya oil, cotton oil, lucerne oil, poppy oil, marrow oil, evening primrose oil, millet oil, barley oil, rye oil, safflower oil, canelle nut tree oil, passion flower oil, hazelnut oil, palm oil, shea butter, apricot kernel oil, Alexandria laurel tree oil, sysymbrium oil, avocado oil, and calendula oil;

modified plant oils such as the products known by the INCI names Apricot Kernel Oil PEG-6 esters and Olive Oil PEG-6 esters;

oils of natural origin, such as perhydrosqualene and squalene;

mineral oils such as paraffin oil ; and mineral oils originating especially from petroleum cuts, such as isoparaffins with boiling points of between 300 and 400° C.; and synthetic oils, especially fatty acid esters such as butyl myristate, propyl myristate, cetyl myristate, isopropyl palmitate, butyl stearate, hexadecyl stearate, isopropyl stearate, octyl stearate, isocetyl stearate, dodecyl oleate, hexyl laurate and propylene glycol dicaprylate; ester derivatives of lanolic acid, such as isopropyl lanolate and isocetyl lanolate; triglycerides such as glycerol triheptanoate; alkyl benzoates; isoparaffins; polyalphaolefins; polyolefins; synthetic isoalkanes such as isohexadecane and isododecane; and silicone oils. Among the latter oils, there may be mentioned more particularly dimethylpolysiloxanes, methylphenylpolysiloxanes, silicones modified by amines, silicones modified by fatty acids, silicones modified by alcohols, silicones modified by alcohols and fatty acids, silicones modified by polyether groups, epoxy-modified silicones, silicones modified by fluorinated groups, cyclic silicones and silicones modified by alkyl groups.

In general terms, the emulsions according to the present invention will comprise up to 50% by weight and preferably between 5 and 30% by weight of oily phase as defined above.

These emulsions can be prepared simply by dispersing a fatty phase, consisting of the above-mentioned composition and optionally one or more oils as described above, in a hydrophilic phase, generally water or a hydrophilic solvent.

The dispersion process can be carried out hot or cold, depending on the melting point of the emulsifying composition, it being necessary for all the constituents to be liquid at the time of mixing.

The emulsions obtained in this way differ from those which can be obtained from the emulsifying compositions of the state of the art in that they are stable and fluid, as will be demonstrated further on, without using a co-surfactant or a stabiliser.

The invention will be illustrated in greater detail by the following Examples, which are given solely by way of illustration.

EXAMPLE 1

Method of preparing a composition based on alkyl polyglycosides and fatty alcohols according to the invention.

A fatty alcohol cut consisting, in percentage by weight, of 16.5% of $C_{12}$ alcohol, 18.5% of $C_{14}$ alcohol, 4.5% of $C_{16-18}$ alcohols and 60.5% of $C_{20-22}$ alcohols, is introduced into a polyvalent reactor.

Glucose is also introduced into a reactor such that the molar ratio between the fatty alcohol and the glucose be: 6/1.

The glucose is then allowed to react with the fatty alcohol for 5 hours at a temperature of about 100°0 C. in the presence of an acid catalyst, under partial vacuum.

After neutralisation of the catalyst, the resulting composition comprises:

80.1% of fatty alcohol,
3.3% of $C_{12}$ APG,
3.7% of $C_{14}$ APG,
0.9% of $C_{16-18}$ APG, and
12.0% of $C_{20-22}$ APG.

COMPARATIVE EXAMPLES 1 to 7

Seven other compositions based on alkyl polyglycosides and fatty alcohols were prepared in order to study notably the influence of the nature of the mixture of alkyl polyglycosides upon the properties obtained.

These compositions were prepared in following the experimental protocol described in Example 1, in selecting the suitable cut of fatty alcohols.

The compositions of the mixtures of alkyl polyglycosides and fatty alcohols thus obtained are mentioned in Table I below.

DEMONSTRATION OF THE PROPERTIES OF THE COMPOSITIONS IN ACCORDANCE WITH THE INVENTION

Various emulsions were produced by means of the compositions of Example 1 as well as of the compositions of Comparative Examples 1 to 7, in order to demonstrate the particular properties of the compositions based on alkyl polyglycosides and fatty alcohols in accordance with the present invention.

These emulsions were prepared in the following way:

A mixture consisting of an emulsifing composition and an oily phase is brought to a temperature greater than the melting point of the alkyl polyglycosides composition, so as to obtain a liquid mixture.

The aqueous phase or a polar solvent is heated to the same temperature.

The two phases (oily and aqueous) are then homogenised by means of a Silverson apparatus, for example for a period of time of 3 to 6 min at 4 000 rpm.

The emulsions are then cooled to ambient temperature under slow, anchor-type agitation.

These emulsions have the following compositions:

| | |
|---|---|
| emulsifying compositions according to the invention or according to a Comparative Example | 3%, |
| fatty phase | 10%, |
| water | 75%. |

Two studies were made to vary the nature of the fatty phase.
Study 1: fatty phase=cetearyl octanoate
Study 2: fatty phase=capric caprylic triglyceride.

The stability of the emulsions thus prepared is monitored after ageing at 40° C.

The viscosity of the emulsions expressed in cP.s is measured after ageing at ambient temperature with the aid of a Brookfield viscosimeter.

The results obtained are given in Table II below:
In this Table:

M signifies: month

DPH signifies: dephasing

D signifies: days.

As Table II shows, the results obtained demonstrate that only the composition of the invention represented by the composition of Example 1 has simultaneously good fluidity and stability properties.

The compositions of the Comparative Examples, although they too consist of mixtures of alkyl polyglycosides and fatty alcohols, do not enable these two properties to be obtained simultaneously, and this demonstrates the critical feature of the compositions according to the invention.

Several examples of stable, fluid emulsions which can be prepared by employing the compositions according to the invention will be given below.

| | |
|---|---|
| Body milk | |
| Composition according to the invention | 3% |
| Alkyl benzoate | 3% |
| Cyclomethicone | 1% |
| Dimethicone | 3% |
| Jojoba oil | 2% |
| Water qsp | 100% |
| Characteristics | |
| Aspect = milk | |
| Viscosity = 3000 mPa.S | |
| pH = 5.7 | |
| Baby toilet milk | |
| Composition according to the invention | 3% |
| Liquid paraffin | 2% |
| Cetearyl octanoate | 3% |
| Sunflower oil | 2% |
| Borage oil | 3% |
| water qsp | 100% |
| Characteristics | |
| Aspect = milk | |
| Viscosity = 4000 mPa.S | |
| pH = 6 | |
| Make-up remover milk | |
| Composition according to the invention | 4% |
| Cetearyl octanoate | 20% |
| Glycerine | 5% |
| water qsp | 100% |
| Characteristics | |
| Aspect = milk | |
| Viscosity = 4500 mPa.S | |
| pH = 7 | |
| After-sun soothing milk | |
| Composition according to the invention | 2.5% |
| SEPICALM ® V6 | 1.0% |
| Isohexadecane | 3% |

TABLE I

| | Comp. ex. 1 | Comp. ex. 2 | Comp. ex. 3 | Comp. ex. 4 | Comp. ex. 5 | Comp. ex. 6 | Ex. 1 | Comp. ex. 7 |
|---|---|---|---|---|---|---|---|---|
| Composition: | | | | | | | | |
| Free fatty alcohols | 76.50% | 75.90% | 81.10% | 77.70% | 76.40% | 75.10% | 80.20% | 84.70% |
| APG | | | | | | | | |
| C12 | 6.5% | 6.5% | 3.3% | 6.5% | 6.5% | 6.5% | 3.3% | |
| C14 | 3.7% | 5.0% | 1.2% | 2.5% | 2.5% | 2.5% | 3.7% | |
| C16–C18 | 1.4% | 1.4% | 1.0% | 1.4% | 2.7% | 4.0% | 0.9% | 1.10% |
| C20–C22 | 13.9% | 11.2% | 13.3% | 11.9% | 11.9% | 11.9% | 12.0% | 14.2% |
| APG Total | 25.5% | 24.1% | 18.8% | 22.3% | 23.6% | 24.9% | 19.9% | 15.3% |
| Study 1 | | | | | | | | |
| Viscosity at D1 | DPH | 1800 | DPH | DPH | DPH | DPH | 2400 | DPH |
| Viscosity at D7 | | 2100 | | | | | 3100 | |
| Viscosity at M1 | | DPH | | | | | 3300 | |
| Viscosity at M3 | | | | | | | 3500 | |
| Study 3 | | | | | | | | |
| Viscosity at D1 | DPH | DPH | DPH | DPH | DPH | DPH | 1300 | DPH |
| Viscosity at D7 | | | | | | | 3000 | |
| Viscosity at M1 | | | | | | | 3400 | |
| Viscosity at M3 | | | | | | | 3500 | |

-continued

| | |
|---|---|
| Squalane | 5% |
| Shea butter | 2% |
| Hazelnut oil | 1% |
| water qsp | 100% |
| Characteristics | |
| Aspect = milk | |
| Viscosity = 5500 mPa.S | |
| pH = 5.5 | |

What is claimed is:

1. Composition based on alkyl polyglycosides and fatty alcohols comprising:
   5 to 60% by weight of a mixture of alkyl polyglycosides consisting essentially of:
   10 to 25% by weight of an alkyl polyglycoside of formula (I):

$$R_1O(G_1)_{x_1} \quad (I),$$

10 to 30% by weight of an alkyl polyglycoside of formula (II):

$$R_2O(G_2)_{x_2} \quad (II),$$

0 to 10% by weight of a mixture of alkyl polyglycosides of formulae (III) and (IV):

$$R_3O(G_3)_{x_3} \quad (III)$$

$$R_4O(G_4)_{x_4} \quad (IV), \text{ and}$$

40 to 80% by weight of a mixture of alkyl polyglycosides of formulae (V) and (VI):

$$R_5O(G_5)_{x_5} \quad (V)$$

$$R_6O(G_6)_{x_6} \quad (VI),$$

in which $R_1, R_2, R_3, R_4, R_5$ and $R_6$ each represent a linear or branched aliphatic radical having 12, 14, 16, 18, 20 and 22 carbon atoms respectively, $G_1, G_2, G_3, G_4, G_5$ and $G_6$ each represent a saccharide residue, $x_1, x_2, x_3, x_4, x_5$ and $x_6$ each represent a number between 1 and 5; and
   95 to 40% by weight of an alcohol selected from the group consisting of:
      at least one alcohol of formula R'OH, in which R' is a linear or branched aliphatic radical having 12 to 22 carbon atoms; and
      a mixture consisting of alcohols the alkyl part of which is identical to the alkyl part $R_1, R_2, R_3, R_4, R_5$ and $R_6$ of the alkyl polyglycosides mentioned above.

2. Compositions of claim 1, wherein the mixture of said alkyl polyglycosides consists essentially of:

10 to 20% by weight of an alkyl polyglycoside of formula (I):

$$R_1O(G_1)_{x_1} \quad (I),$$

15 to 25% by weight of an alkyl polyglycoside of formula (II):

$$R_1O(G_2)_{x_2} \quad (II),$$

0 to 10% by weight of a mixture of alkyl polyglycosides of formulae (III) and (IV):

$$R_3O(G_3)_{x_3} \quad (III)$$

$$R_4O(G_4)_{x_4} \quad (IV), \text{ and}$$

50 to 70% by weight of a mixture of alkyl polyglycosides of formulae (V) and (VI):

$$R_5O(G_5)_{x_5} \quad (V)$$

$$R_6O(G_6)_{x_6} \quad (VI).$$

3. Composition of claim 1 comprising:
   10 to 40% by weight of a mixture of alkyl polyglycosides as defined in claim 1, and
   90 to 60% by weight of at least one said alcohol.

4. Composition of claim 1 comprising:
   19.9% by weight of a mixture of alkyl polyglycosides consisting essentially of:
   17% by weight of an alkyl polyglycoside of formula (I):

$$R_1O(G_1)_{x_1} \quad (I),$$

19% by weight of an alkyl polyglycoside of formula (II):

$$R_2O(G_2)_{x_2} \quad (II),$$

5% by weight of a mixture of alkyl polyglycosides of formulae (III) and (IV):

$$R_3O(G_3)_{x_3} \quad (III)$$

$$R_4O(G_4)_{x_4} \quad (IV), \text{ and}$$

59% by weight of a mixture of alkyl polyglycosides of formulae (V) and (VI):

$$R_5O(G_5)_{x_5} \quad (V)$$

$$R_6O(G_6)_{x_6} \quad (VI),$$

in which $R_1, R_2, R_3, R_4, R_5$ and $R_6$ each represent a linear or branched aliphatic radical having 12, 14, 16, 18, 20 and 22 carbon atoms respectively, $G_1, G_2, G_3, G_4, G_5$ and $G_6$ each represent a saccharide residue, $x_1, x_2, x_3, x_4, x_5$ and $x_6$ each represent a number between 1 and 5; and
   80.1% by weight of an alcohol selected from the group consisting of:
      at least one alcohol of formula R'OH, in which R' is a linear or branched aliphatic radical having 12 to 22 carbon atoms; and
      a mixture consisting of alcohols the alkyl part of which is identical to the alkyl part $R_1, R_2, R_3, R_4, R_5$ and $R_6$ of the alkyl polyglycosides mentioned above.

5. Stable, fluid emulsion comprising at least an aqueous phase and an oily phase and, as main emulsifier, a composition based on alkyl polyglycosides and fatty alcohols as defined in claim 1.

6. Emulsion of claim 5 comprising 1 to 25% by weight of said emulsifying composition and up to 50% by weight of said oily phase.

7. Emulsion of claim 5 comprising 1 to 10% by weight of said emulsifying composition and up to 50% by weight of said oily phase.

* * * * *